United States Patent
Hedgecock et al.

(12) 
(10) Patent No.: US 6,329,383 B1
(45) Date of Patent: Dec. 11, 2001

(54) 2-AMINO-5-PYRIMIDINE ACETIC ACID COMPOUNDS

(75) Inventors: Charles Hedgecock, Uppsala; Eric Desarbre; Guido Kurz, both of Stockholm; Martin Norin, Bromma; Marguerite Luthman, Lidingö; Cathrin Widerståhl, Bromma, all of (SE)

(73) Assignee: Pharmacia AB, Stockholm (SE)

( * ) Notice: Subject to any disclaimer, the term of this patent is extended or adjusted under 35 U.S.C. 154(b) by 0 days.

(21) Appl. No.: 09/490,232

(22) Filed: Jan. 24, 2000

Related U.S. Application Data

(60) Provisional application No. 60/118,973, filed on Feb. 8, 1999.

(30) Foreign Application Priority Data

Jan. 25, 1999 (SE) .................................................... 9900211

(51) Int. Cl.[7] ..................... C07D 403/12; C07D 413/12; C07D 417/12; A61K 31/506; A61P 5/06

(52) U.S. Cl. .......................... 514/272; 514/275; 544/320; 544/331

(58) Field of Search .................... 514/272, 275, 514/269; 544/320, 331

(56) References Cited

PUBLICATIONS

Streitwieser, A. and Heathcock, C.H., "Introduction to Organic Chemistry, 2nd Ed.", Macmillan, New York, 1981, p. 649.*

Singh, S.P.; Prakash, Indra; Tomer, R. K.; Prakash, O. M.; Sawhney, S. N., Indian J. Chem., Sect. B, 22B(1), 37–42, 1983.*

Singh et al, *Indian Journal of Chemistry*, 22B:37–42 (Jan. 1983).

* cited by examiner

*Primary Examiner*—Mukund J. Shah
*Assistant Examiner*—Thomas C McKenzie
(74) *Attorney, Agent, or Firm*—Dinsmore & Shohl LLP

(57) ABSTRACT

The present invention relates to new benzimidazole compounds with the following general structure (I):

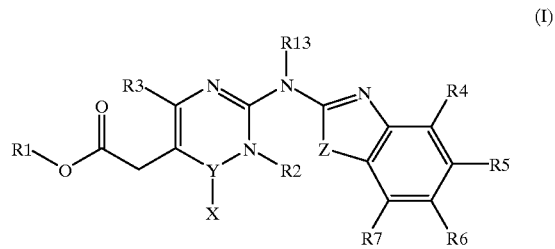

(I)

in which

Y—X is >C=X when X is NR8, O, or S and R2 is H, alkyl, substituted alkylaryl or substituted aryl; or Y—X is >C—X when X is H, alkyl, substituted alkyl, aryl, substituted aryl, OR9 or NHR9 and R2 is a bond to Y;

Z is O, S or NR12;

R1 is H, alkyl, substituted alkyl, aryl or substituted aryl;

R3 is H, alkyl, substituted alkyl, aryl or substituted aryl, OR9 or NHR9;

R4, R5, R6 and R7 are H, halogen, OR10, NR10, R11, NO2, CF3, CN, COR8, COOR8, CONHR8 and/or N3 in any combination and/or two adjacent R4, R5, R6 or R7 form a carbocyclic or heterocyclic ring; and R8, R9, R10, R11, R12 and R13 are H, alkyl, substituted alkylaryl, aryl and/or substituted aryl in any combination.

These compounds are useful as a human Growth Hormone (hGH) mimetic, which trigger GH agonist effects in animals and especially as an orally available human Growth Hormone (hGH).

26 Claims, 5 Drawing Sheets

Scheme II

Scheme III

Scheme IV

Scheme V

Dose response curves of hGH and (2) in dimerisation assay

Glucose uptake in cardiac myocytes treated with medium (control), hGH (x nM) and (2) (10 mM)

2-AMINO-5-PYRIMIDINE ACETIC ACID COMPOUNDS

RELATED APPLICATION

This application claims the benefit of U.S. Provisional Application No. 60/118,973 filed Feb. 8, 1999.

FIELD OF THE INVENTION

The present invention relates to new benzimidazole compounds with the following general structure (I):

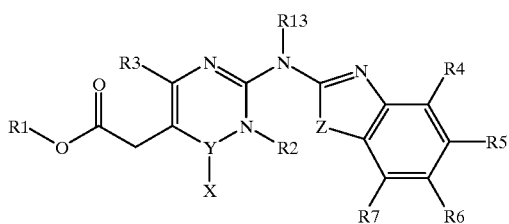

in which

Y—X is >C=X when X is NR8, O, or S and R2 is H, alkyl, substituted alkylaryl or substituted aryl; or Y—X is >C—X when X is H, alkyl, substituted alkyl, aryl, substituted aryl, OR9 or NHR9 and R2 is a bond to Y;

Z is O, S or NR12;

R1 is H, alkyl, substituted alkyl, aryl or substituted aryl;

R3 is H, alkyl, substituted alkyl, aryl or substituted aryl, OR9 or NHR9;

R4, R5, R6 and R7 are H, halogen, OR10, NR10, R11, NO2, CF3, CN, COR8, COOR8, CONHR8 and/or N3 in any combination and/or two adjacent R4, R5, R6 or R7 form a carbocyclic or heterocyclic ring; and R8, R9, R10, R11, R12 and R13 are H, alkyl, substituted alkylaryl, aryl and/or substituted aryl in any combination.

One compound included in formula I is known to have anti-inflammatory activity, and this is the compound in which R1 is $C_2H_5$, Y—X is >C—OH, Z is N, and R2, R3, R4, R5, R6, R7 and R13 are H.

The compounds included in formula I are useful as a human (Growth Hormone (hGH) mimetic, which trigger GH agonist effects in animals and especially as an orally available human Growth Hormone (hGH).

BACKGROUND hGH is a protein consisting of a single chain of 191 amino acids. The molecule is cross-linked by two disulphide bridges and the monomeric form has a molecular weight of 22 kDa. Recombinant hGH (22 kDa) has been commercially available for several years. It is preferred over the pituitary derived products because the product prepared from human tissue might contain infectious agents such as that for the Creutzfeldt-Jacob's disease. Two types of therapeutically useful recombinant hGH preparations are present on the market: the natural sequence, e.g. Genotropin®, Kabi Pharmacia AB, and an analogue with an additional methionine residue at the N-terminal end, e.g. Somatonorm®. hGH is used to stimulate linear growth in patients with hypopituitary dwarfism or Turner's syndrome but other indications have also been suggested. The protein hGH must be administered by injection and there is a need for an oral available compound with the same biological activity as the natural occuring GH. The benzimidazoles falling under the general formula I are new with one exception i.e. the compound in formula I in which R1 is $C_2H_5$, Y—X is >C—OH, Z is N and R2, R3, R4, R5, R6, R7 and R13 are H. That compound is known to have anti-inflammatory activity from Singh et al. Indian J of Chemistry. Vol 22B, January 1983. 37–42. (Compound IId, IIp and IIu in Table 1).

SUMMARY OF THE INVENTION

We have unexpectedly found a group of compounds having the biological activity of growth hormone and which could be useful as alternatives to recombinant and native growth hormone.

A number of compounds have been identified. e.g. 2-[(5, 6-Dimetlhyl-2-benzoimidazolyl)amino]-4-hydroxy-6-methyl-5-pyrimidine acetic acid (2) and 2-[(5,6-Dimethyl-2-benzoimidadazolyl)amino]-4-hydroxy-6-methyl-5-pyrimidine acetic acid, ethyl ester (1). (1) is found to be a selective agonist for the growth hormone receptor against the closely related prolactin receptors which is of importance when looking for a specific growth hormone mimetic.

The invention thus relates to compounds with the general structure (I):

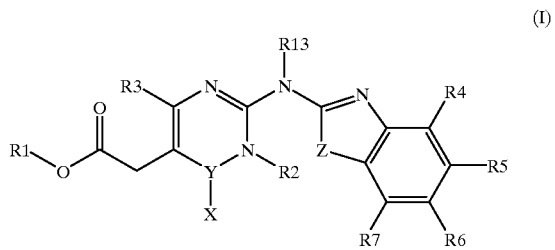

in which

Y—X is >C=X when X is NR8, O, or S and R2 is H, alkyl, substituted alkylaryl or substituted aryl; or Y—X is >C—X when X is H, alkyl, substituted alkyl, aryl, substituted aryl, OR9 or NHR9 and R2 is a bond to Y;

Z is O, S or NR12;

R1 is H, alkyl, substituted alkyl, aryl or substituted aryl;

R3 is H, alkyl, substituted alkyl, aryl or substituted aryl, OR9 or NHR9;

R4, R5, R6, and R7 are H, halogen, OR10, NR10, R11, NO2. CF3, CN, COR8, COOR8, CONHR8 and/or N3 in any combination and/or two adjacent R4, R5, R6 or R7 form a carbocyclic or heterocyclic ring; and R8, R9, R10, R11, R12 and R13 are H, alkyl, substituted alkylaryl, aryl and/or substituted aryl in any combination with the proviso that R1 is not $C_2H_5$ when Y—X is >C—OH, Z is N R12 and R2, R3, R4, R5, R6, R7 and R13 are H.

By alkyl is meant a straight or branched chain with 1 to 8 carbton atoms, preferably 1 to 4 carbon atoms, e.g. methyl, ethyl, propyl, bultyl and isoforms thereof.

By aryl is preferably meant a ring having 5–12 carbon atoms, e.g. cyclopropyl, phenyl, cyclohexyl and possibly one or two hetero atoms.

By "substituted" is preferably meant a substitution by halogen, —OH, alkyl OR10, NR10, R11, NO2, CF3, CN, COR8 and/or COOR8.

By "hetero atom" is preferably meant O, S and/or N.

The compounds could be a pharmaceutical acceptable salts and esters thereof.

More particular the following compounds are of interest:

2-[(5,6-Dimethyl-2-benzoimidazolyl)amino]-4-hydroxy-6-methyl-5-pyrimidine acetic acid, ethyl ester (1) and 2-[(5,6-Dimethyl-2-benzoimidazolyl)amino]-4-hydroxy-6-methyl-5-pyrimidine acetic acid (2).

The invention also relates to use of the claims compounds, pharmaceutical compositions comprising the compounds and method for the preparation of the compounds as claimed.

We have shown biological activity for the claimed compounds by different assays, such as a dimerisation assay in which the compounds which mimics the quench induced upon hGH binding in this assay also may mimic the full biological effects of native hormone and increased glucose transport.

The claimed compounds can be useful for treatment of diseases related to e.g. growth hormone deficiency, Turner syndrome, infertility, wound healing, dystrophy, osteoporosis, and/or lactation failure, for preoperative administration and other diseases and conditions which are treated or could be treated by administration of hGH.

DETAILED DESCRIPTION

Figure 1A:
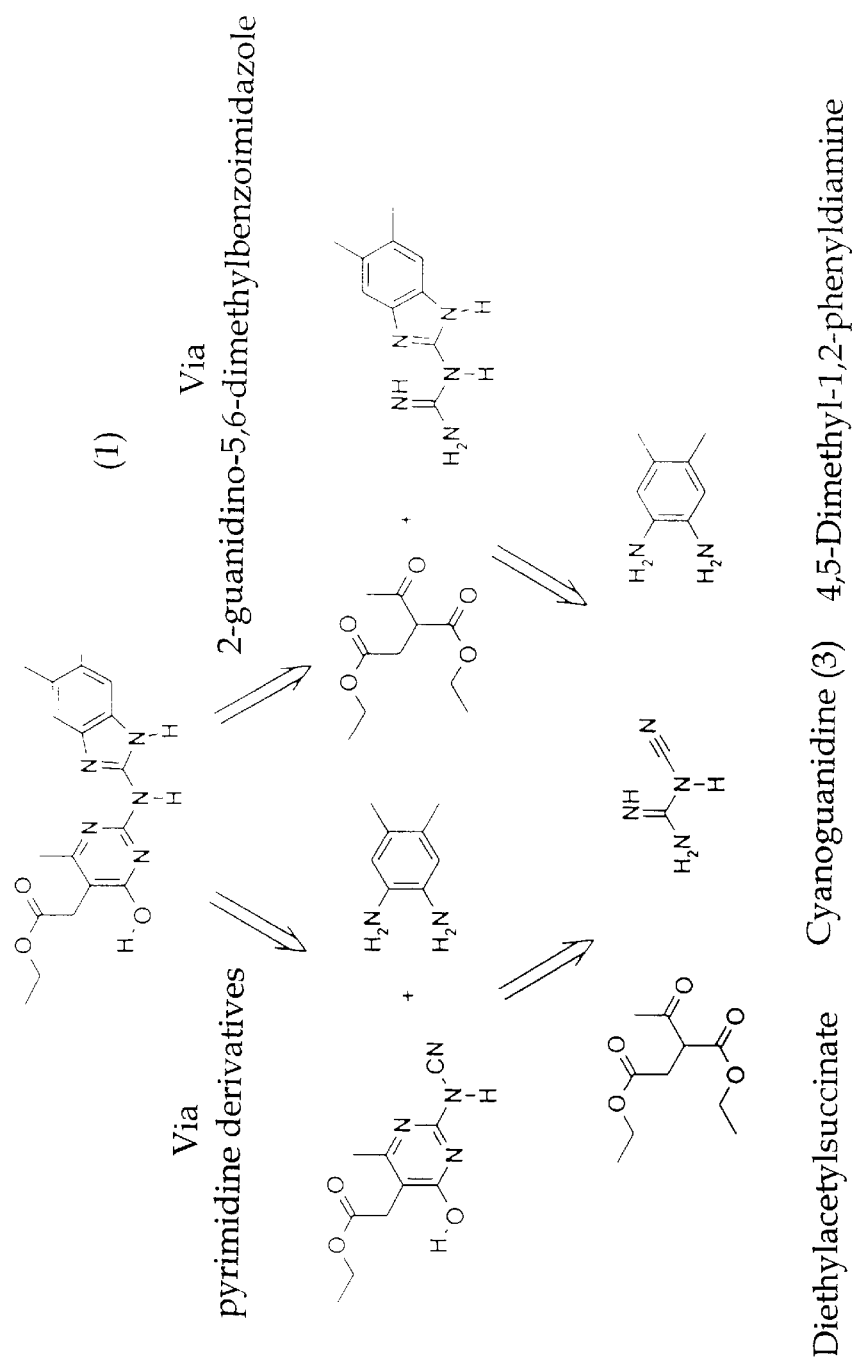
FIGS. 1A and 1B illustrate Schemes I and II, respectively.
Figure 1B:
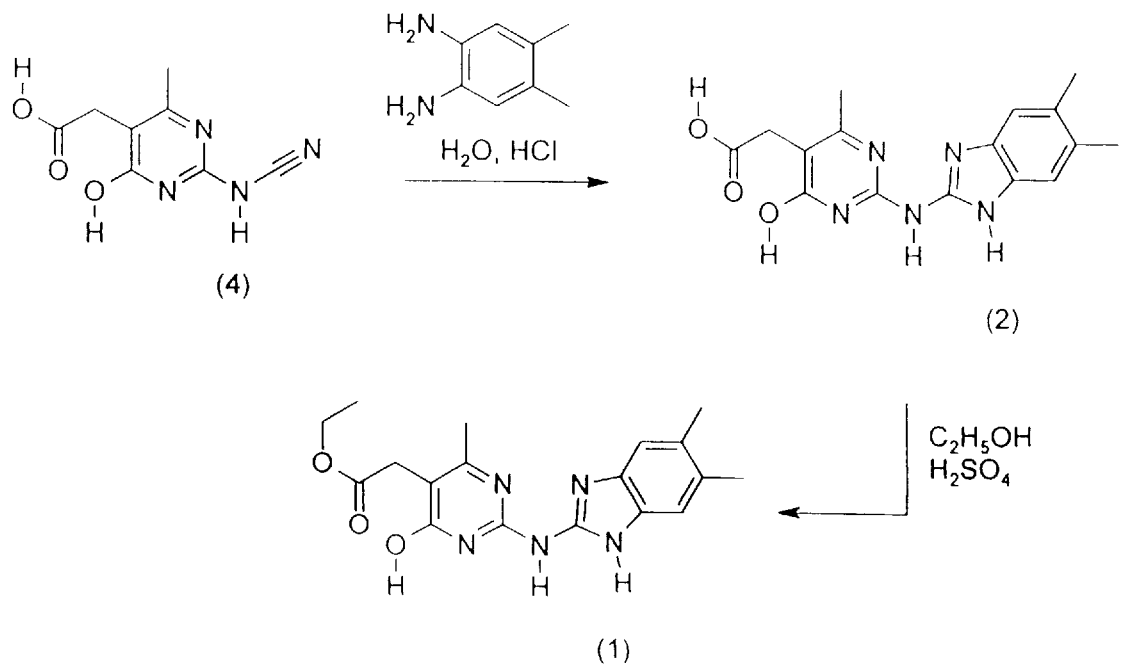
Figure 2:
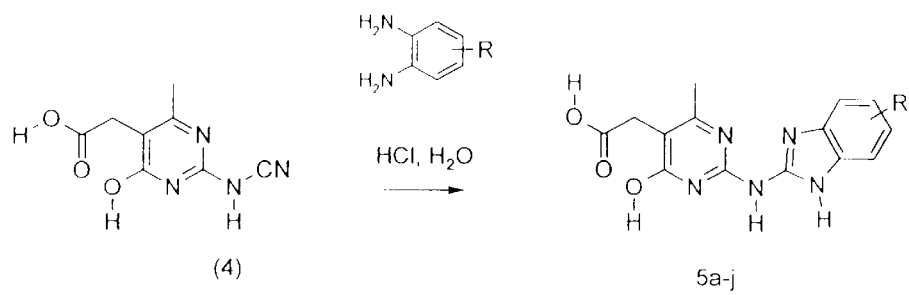
FIG. 2 illustrates Schemes III, IV and V.
Figure 2:
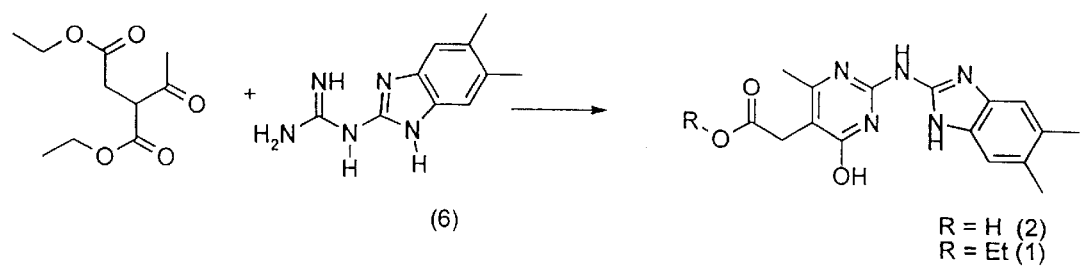
Figure 2:
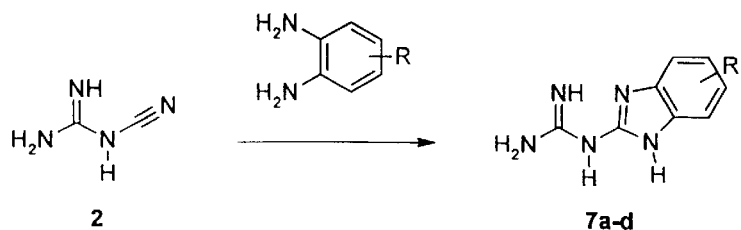

These compounds can be prepared according to two different routes:
1) via pyrimidine derivatives or
2) via the 2-guanidino-5,6-dimethylbeinzoimidazole See FIG. 1. scheme I.

Preparation of 2-[(5,6-Dimethyl-2-benzoimidazolyl)amino]-4-hydroxy-6-methyl-5-pyrimidine acetic acid, ethyl ester (1) and Analogues 1) Via pyrimidine derivatives (2-Cyanoamino)-4-hydroxy-6-methyl-5-pyrimidine acetic acid (4) obtained from diethyl acetylsuccinate and cyanoguanidine in presence of sodium in ethanol, was treated with phenyldiamine in $H_2O$ and concentrated HCl to afford 2-[(5,6-Dimethyl-2-benzoimidazolyl)amino]-4-hydroxy-6-methyl-5-pyrimidine acetic acid (2) in 25% yield. Recrystallisation of acid from DMF gave the pure compound. Esterification was performed in ethanol in presence of $H_2SO_4$ to lead to 2-[(5,6-Dimethyl-2-benzoimidazolyl)amino]-4-hydroxy-6-methyl-5-pyrimidine acetic acid, ethyl ester (1) in only 19% yield (scheme II).

Synthesis of analogues 5a–j was carried out similarly by reacting (4) with different ortho-diamino derivatives, under the conditions used to prepare (2), as shown in scheme III.

The following compounds were prepared according to Scheme II or III:

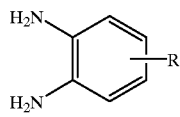 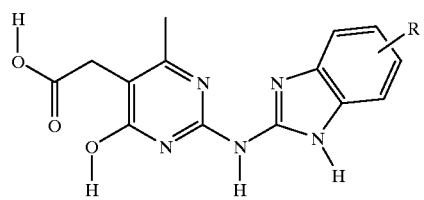

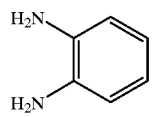 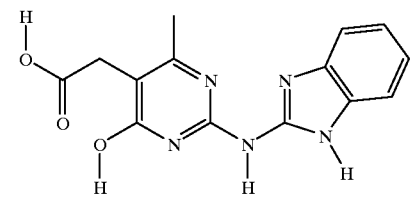

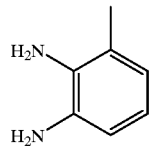 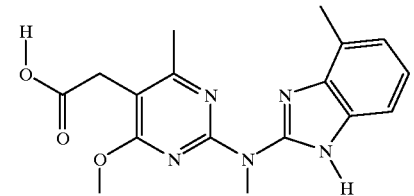

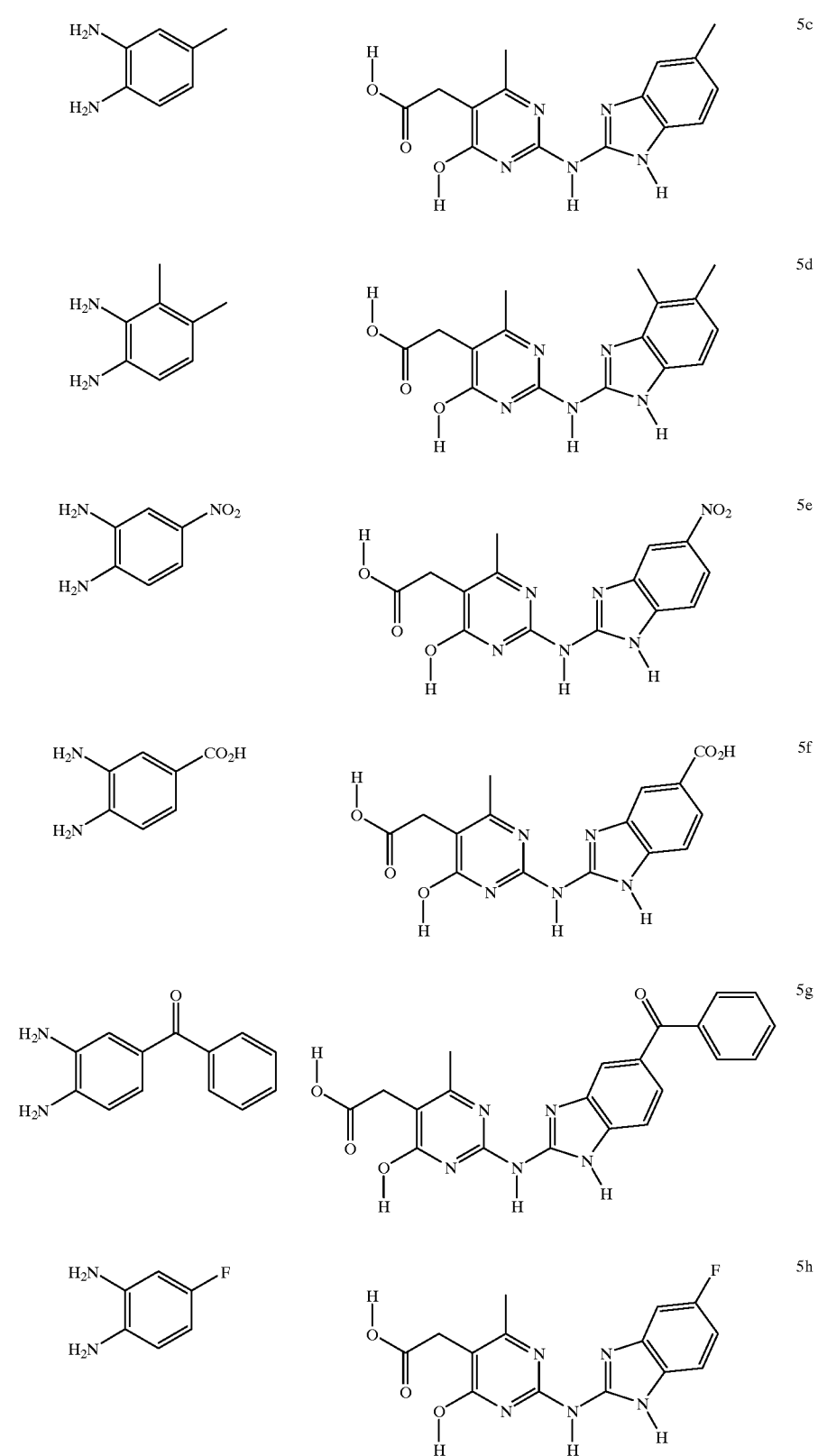

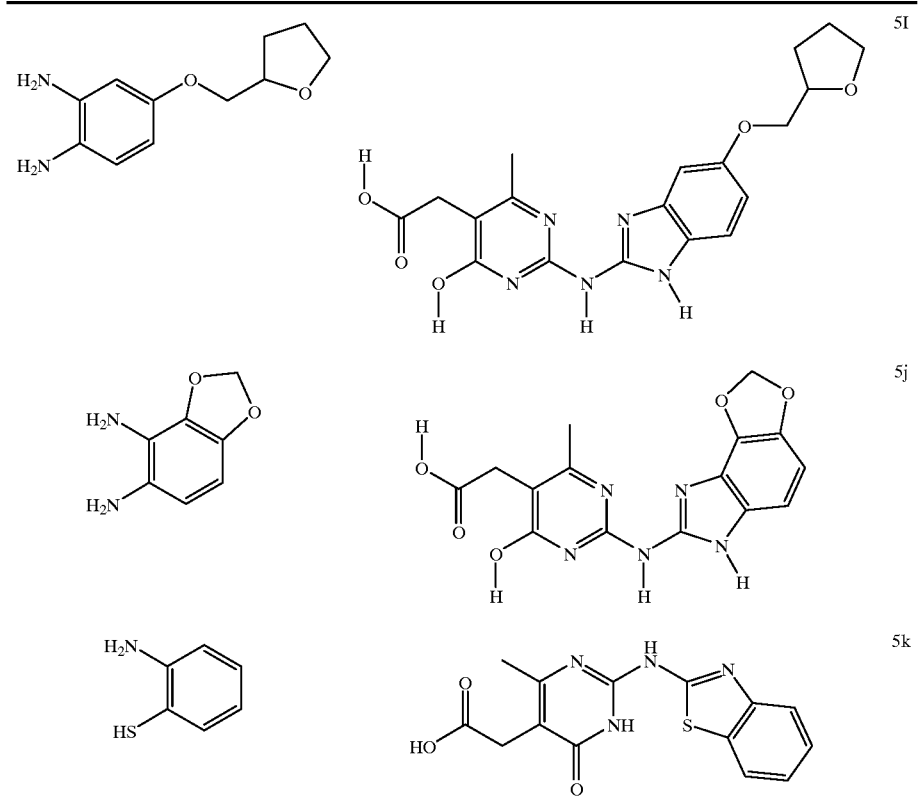

The reaction was carried in refluxing $H_2O$ for 2 hours then cooled to room temperature and the precipitate was collected. Similarly benzothiazole analogues can be prepared. Thus 5k was prepared from the corresponding aminiothioplhenol in 3M HCl at 100° C./10 hr, to give the product in 40% yield after recystallisation.

2) Via 2-guanidino-benzoimidazoles, scheme IV.

The parent acid (2) was obtained in 27% yield when 2-guanidino-5,6-dimethylimidazole 2-guanidino-5,6-dimethyl-benizidazole, (6) was heated at 120° C. for 45 min in neat diethyl acetylsuccinate, followed by refluxing in ethanol and recrytallisation from DMF.

In order to prepare a number of analogues of (2) by this route a series of 2-guanidinobenzoimidazoles were prepared (scheme V).

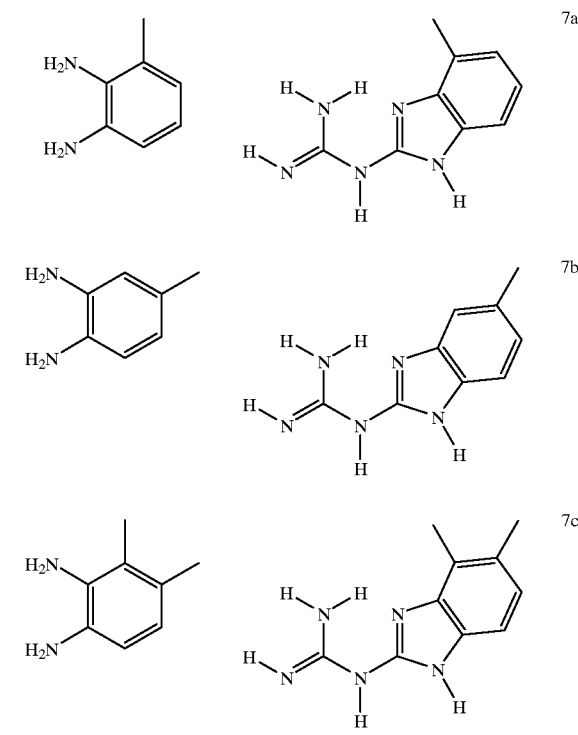

-continued

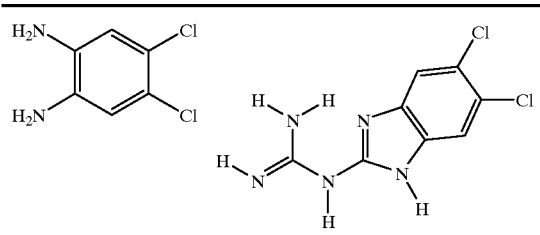

Similarly heating 2-guanidinobenzothiazole and ethyl acetoacetate together at 110° C. for 45 min gave (8)

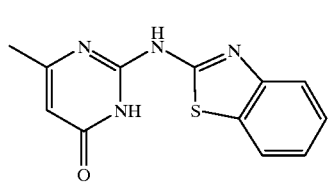

(8)

Preparation of 6-Alkyl analogues of 2-[(5,6-Dimethyl-2-benzoimidazolyl)amino]-4-hydroxy-6-methyl-5-pyrimidine acetic acid (2)

These analogues were prepared in a similar fashion to (2)

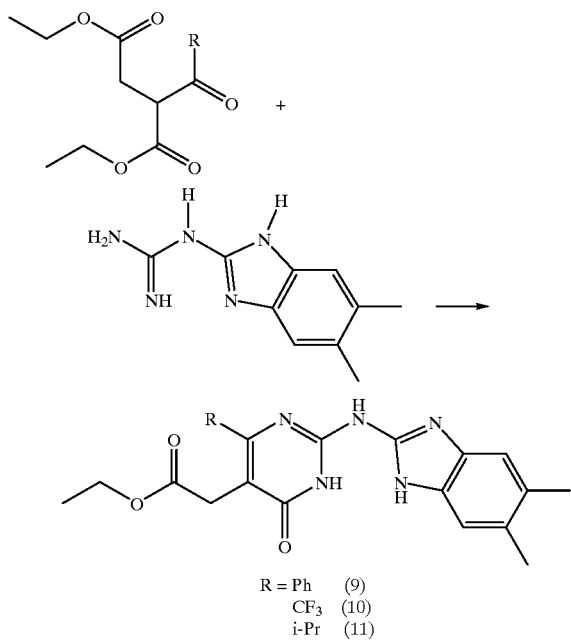

R = Ph (9)
CF$_3$ (10)
i-Pr (11)

Preparation of N-1 Alkyl Analogues of (2)

N-1 methyl analogues could be prepared in low yield during the methylation of the dithiocarbonimido using excess methyl iodide.

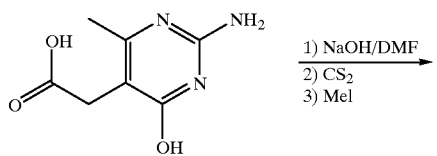

-continued

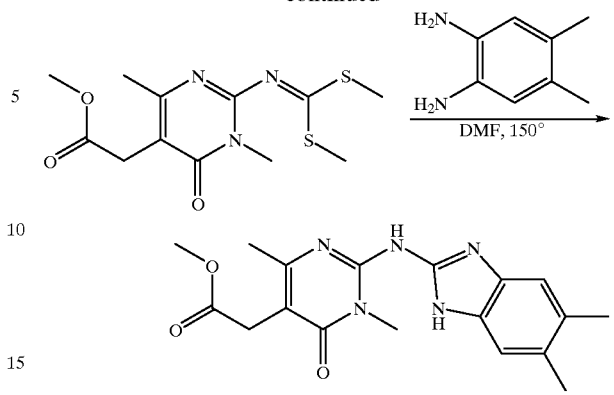

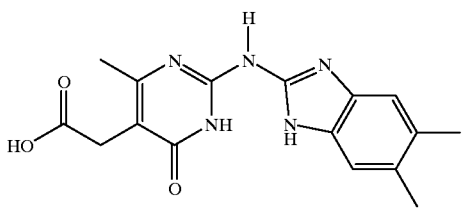

(12)

EXAMPLES

Example 1

2-[(5,6-Dimethyl-2-benzoimidazolyl)amino]-4-hydoxy-6-methyl-5-pyrimidine acetic acid (2)

Under an inert atmosphere, Na (2-(Cyanoamino)-4-hydroxy-6-methyl-5-pyrimidine acetic acid (4) (0.345 g, 15 mmol) was added portionwise to dry ethanol (10 ml) at room temperature. After stirring for 15 min (disappearance of the Na), cyanoguanidine (0.840 g, 10 mmol) and diethyl acetylsuccinate (2.0 mL, 10 mmol) were added to the solution at room temperature.

The suspension was heated at reflux for 5 h and the resulting suspension was cooled, filtered and washed with ethanol. The precipitate was dissolved in water (at the solubility limit) and concentrated HCl was added. The precipitate formed was filtered and gave 1.10 g (50%) of Na (2-Cyanoamino)-4-hydroxy-6-methyl-5-pyrimidine acetic acid. mp: 234–236° C. (dec). IR (KBr): υ=3520, 3440, 3200–2500. 2190, 1730, 1655, 1602, 1500, 1340, 1200, 830 cm$^{-1}$.

(2-Cyanoamino)-4-hydroxy-6-methyl-5-pyrimidine acetic acid (4) (0.416 g, 2 mmol) and 5,6-dimethyl-1,2-diphenyldiamine (0.276 g, 2 mmol) in a mixture of H$_2$O (2 mL) and concentrated HCl (0.4 mL) were stirred for 1.5 h at 100° C. The initial suspension dissolved and a second precipitate appeared after 1 h. The suspension was cooled and the precipitate was collected and washed with water to give 0.164 g (25%) of 2-[(5,6-Dimethyl-2-bezoimidazolyl)amino]-4-hydroxy-6-methyl-5-pyrimidine acetic acid (2). mp: >300° C. (DMF). IR (KBr): υ=3331, 2949, 1705, 1655, 1602, 1509, 1252, 1157, 1047, 701 cm$^{-1}$. Accurate mass: calculated: 327.1331. Found 327.1337. Analysis calculated for C$_{16}$H$_{17}$N$_5$O$_3$: C, 58.71; H, 5.23; N, 21.39. Found: C, 57.8; H, 5.1; N. 20.7.

Example 2

2-[(5,6-Dimethyl-2-benzoimidazolyl)amino]-4-hydroxy-6-methyl-5-pyrimidine acetic acid, ethyl ester (1)

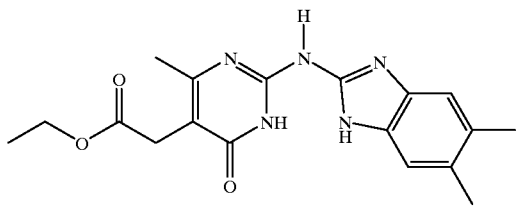

A solution of (2) (0.935 g, 2.86 mmol) in ethanol (20 mL) and concentrated $H_2SO_4$ (3.5 mL) was heated at reflux for 24 h. The ethanol was evaporated in vacuo, cold water (30 mL) was added and the solution was then neutralised with NaOH 10M. The mixture was extracted with $CHCl_3$ (4×20 ml,) and the combined organic phases were dried ($MgSO_4$) and evaporated in vacuo. The resulting residue was triturated with ethanol and filtered to give 0.190 g (19%) of 2-[(5,6-Dimetlhyl-2-benzoimidazolyl)amino]-4-hydroxy-6-methyl-5-pyrimidine acetic acid, ethyl ester (1). mp: >300° C. ($CF_3CO_2H/C_2H_5OH$). IR (KBr): $\upsilon$=3254, 2968, 2922, 1737, 1623, 1560, 1344, 1294, 774 cm$^{-1}$. Accurate mass: calculated: 355.1644. Found 327.1644. Analysis calculated for $C_{18}H_{21}N_5O_3$: C, 60.83; H, 5.96; N, 19.71. Found: C, 60.1; H, 5.7; N, 18.7.

Example 3

2-[(2-benzoimidazolyl)amino]-4-hydroxy-6-methyl-5-pyrimidine acetic acid (5a)

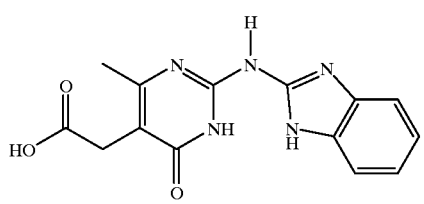

(5a) was prepared according to procedure used for (2) in Example 1; yield 5%. mp: >300° C. (DMF). IR (KBr): $\upsilon$=2878, 1748. 1700, 1625, 1557, 1474, 1357, 1219, 744 cm$^{-1}$. $^1$H-NMR ($CF_3CO_2D$): δ=2.64 (s, 3H, $CH_3$), 3.88 (s, 2H, $CH_2$), 7.52 (m, 2H, 2×H$_{arom}$), 7.67 (m, 2H, 2×H$_{arom}$). Accurate mass: calculated: 299.1018. Found 299.1013. Analysis calculated for $C_{14}H_{13}N_5O_3$: C, 55.2; H, 4.40; N, 23.40. Found: C. 55.4; H, 4.7; N, 22.5.

Example 4

2-[(4-methyl-2-benzoimidazolyl)amino]-4-hydroxy-6-methyl-5-pyrimidine acetic acid (5b)

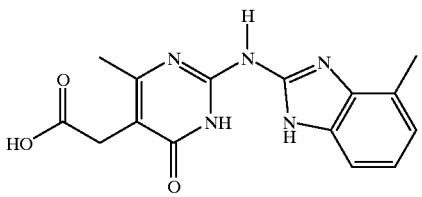

L-112787 was prepared according to procedure used for (2) in Example 1; yield 1%. mp: >300° C. (DMF). IR (KBr): $\upsilon$=3150–2700, 1701, 1638, 1605, 1570, 1419, 1353, 1228, 781 cm$^{-1}$. Accurate mass: calculated: 313.1175. Found 313.1190. Analysis calculated for $C_{15}H_{15}N_5O_3$: C, 57.50; H, 4.83; N, 22.35. Found: C, 53.3; H, 4.5; N, 20.4.

Example 5

2-[(5-methyl-2-benzoimidazolyl)amino]-4-hydroxy-6-methyl-5-pyrimidine acetic acid (5c)

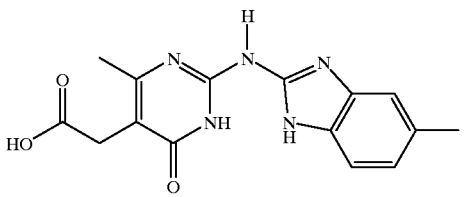

L-112788 was prepared according to procedure used for (2) in Example 1; yield 5%. mp: >300°° C. (DMF). IR (KBr): $\upsilon$=3200–2700, 1702, 1640, 1602, 1474, 1352, 1295, 1207, 875, 796 cm$^{-1}$. Accurate mass: calculated: 313.1175. Found 313.1187. Analysis calculated for $C_{15}H_{15}N_5O_3$: C, 57.50; H, 4.83; N, 22.35. Found: C, 53.3; H, 4.5; N, 20.4.

Example 6

2-[(4,5-dimethyl-2-benzoimidazolyl)amino]-4-hydoxy-6-methyl-5-pyrimidine acetic acid (5d)

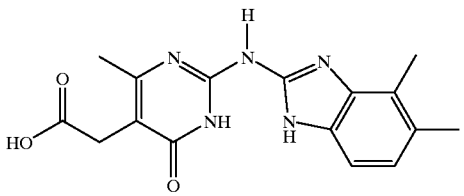

L-112789 was prepared according to procedure used for (2) in Example 1; yield 4%. mp: >300° C. (DMF). IR (KBr): $\upsilon$=3200–2700, 1703, 1627, 1601, 1565, 1342, 1293, 1234, 903, 788 cm$^{-1}$. Accurate mass: calculated: 327.1331. Found 327.1349.

Example 7

2-[(5-nitro-2-benzoimidazolyl)amino]-4-hydroxy-6-methyl-5-pyrimidine acetic acid (5c)

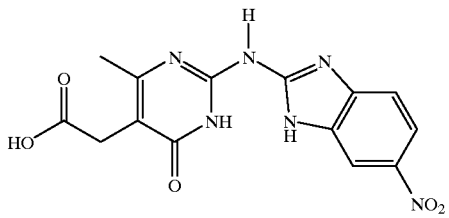

PNU-181223 was prepared according to procedure used for (2) in Example 1; yield 16%. mp: >300° C. (DMF). IR (KBr): υ=3039, 2882, 1738, 1596, 1465, 1333, 1292, 1182, 876 cm$^{-1}$. $^1$H-NMR (CF$_3$CO$_2$D): δ=2.62 (s, 3H, CH$_3$), 3.87 (s, 2H, CH$_2$), 7.88 (d, 1H, J=8 Hz, H$_{arom}$), 8.45 (d, 1H, J=8 Hz, H$_{arom}$), 7.88 (s, 1H, H$_{arom}$). Analysis calculated for C$_{14}$H$_{12}$N$_6$O$_5$: C, 55.2; H, 4.40; N. 23.40. Found: C, 55.4; H, 4.7; N, 22.5.

Example 8

2-[(5-fluoro-2-benzoimidazolyl)amino]-4-hydroxy-6-methyl-5-pyrimidine acetic acid (5h)

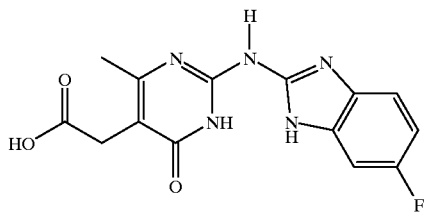

L-112790 was prepared according to procedure used for (2) yield 3%: >300° C. (DMF). IR (KBr): υ=3150–2700, 1625, 1603, 1559, 1484, 1346, 1297, 1145, 790 cm$^{-1}$. Accurate mass: calculated: 317.0924. Found 317.0939. Analysis calculated for C$_{14}$H$_{12}$FN$_5$O$_3$: C, 53.00; H, 3.81; N, 22.07. Found: C, 49.5; H, 4.0; N, 19.9.

Example 9

2-(2'-Benzothiazolylamino)-4-hydroxy-6-methyl-5-pyrimidylacetic acid (5k)

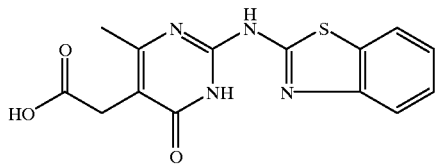

A mixture of 2-aminothiophenol (601.4 mg, 4.80 mmol) and 2-cyanamino-4-hydroxy-6-methyl-5-pyrimidylacetic acid (1.0 g 4.80 mmol) in concentrated HCl (1 mL) and water (5 mL) was stirred at 100° C. for 10 h. The reaction mixture was cooled and the precipitate was filtered and washed with aqueous ethanol. Crude yield 1.2 g (contains minor impurities according to $^1$H NMR). The crude solid was recrystallized from DMF (~150 mL). The product precipitated in the refrigerator. The crystals were triturated with water/MeOH and dried under vaccum at 90° C. (yield 604.5 mg 40%). mp>300° C. $^1$H NMR (CF$_3$COD) d 7.97–7.86 (m, 2H), 8.00–7.54 (m, 4 H), 3.90 (s, 3 H), 2.66 (s, 3 H); Anal. Calcd for C$_{14}$H$_{12}$N$_4$O$_3$S. 0.25 H$_2$O: C, 51.67; H, 4.03; N, 17.22; Found: C, 51.80: H, 3.90; N, 16.95.

Example 10

Benzimidazol-2-yl guanidino derivatives: General procedure for the intermediates In water (8 mL), concentrated HCl (3 mL), cyanoguanidine (20 mmol) and tile orthophenylenediamine derivative (10 mmol) were heated at reflux overnight. A precipitate appeared after cooling, the solid was filtered and washed with water. A suspension, of the solid in water, was treated with a solution of NaOH 1M to reach pH 10. Then the basic Solution was (pH 6) with an aqueous solution of HCl 1M and the resulting precipitate was filtered to give the title compound.

Example 10a

2-Guanidino-4-methylbenzimidazole, hydrochloric salt (7a)

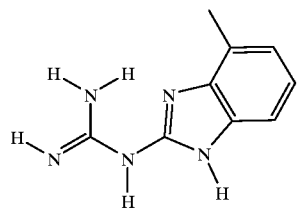

mp: >260° C. IR (KBr): υ=3500–2800, 1616, 1283, 1224, 1159, 963, 764, 729 cm$^{-1}$. Analysis calculated for C$_9$H$_{11}$N$_5$, HCl+½ H$_2$O: C, 46.00; H, 5.5; N, 29.8. Found: C, 46.0; H, 5.7; N, 29.7.

Example 10b

2-Guaniidino-5-methylbenzimidazole, hydrochloric salt (7b)

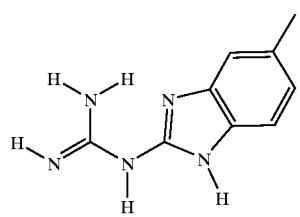

mp: >260° C. IR (KBr): υ=3500–2800, 1667, 1598, 1517, 1487, 1382, 1127, 1037, 802, 782, cm$^{-1}$. Analysis calculated for C$_9$H$_{11}$N$_5$, ½ HCl: C, 52.00; H, 5.54; N, 33.73. Found: C, 51.6; H, 5.5; N, 34.9.

Example 10c

2-Guanidino-4,5-dimethylbenzimidazole, hydrochloric salt (7c)

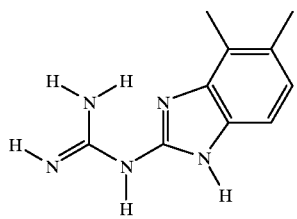

mp: >260° C. IR (KBr): υ=3500–2800, 3361, 1680, 1608, 1573, 1497, 1309, 1270, 1225, 1148, 1054, 791, 748, 723 cm$^{-1}$. Analysis calculated for $C_{10}H_{13}N_5$ HCl+½ $H_2O$: C, 48.3; H, 6.0; N, 28.2. Found: C, 47.9; H, 5.9; N, 29.5.

Example 10d

2-Guanidino-5,6-dichlorobenzimidazole, hydrochloric salt (7d)

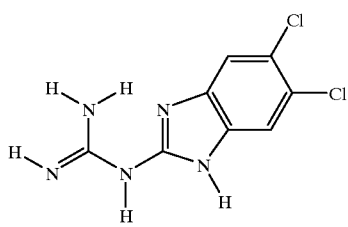

mp: >260° C. IR (KBr): υ=3623, 3496, 3500–2800, 1704, 1622, 1565, 1426, 1280, 1096, 862, 852 cm$^{-1}$. Analysis calculated for $C_8H_7Cl_2N_5$, HCl: C, 34.20; H, 2.85; N, 24.95. Found: C, 34.2; H, 3.3; N, 23.7.

Example 10e 2-(2'-Benzothiazolylamino)-4-hydroxy-6-methylpyrimidine (8)

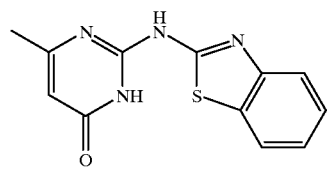

2-(Guanidinobenzothiazole (0.384 g, 2 mmol) and ethyl acetoacetate (2 mL) were heated together at 110° C. lor 45 min. After cooling, ethanol was added, and the resulting precipitate was filtrated to afford 0.050 g (10%) of the title compound. mp: >300° C. IR (KBr): υ=3026, 2867, 1644, 1017, 1590, 1546, 1459, 1360, 762, 742 640 cm$^{-1}$. Analysis calculated for $C_{12}H_{10}N_4OS$: C, 55.8, H, 3.90; N, 21.69. Found: C, 55.2; H, 4.2: N, 22.2.

Example 11

2-[(5,6-Dimetlyl-2-benzoimidazolyl)amino]-4-hydroxy-6-phenyl -5-pyrimidine actic acid, (9)

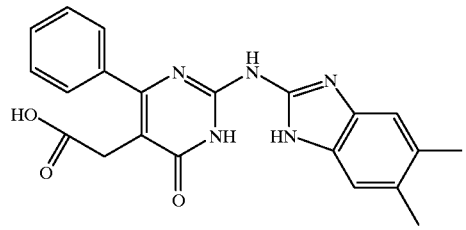

Diethyl-2-benzoyl succinate (2.70 g, 9.7 mmol) and 2-guanidino-5,6-dimethyl-benzimidazole, PNU-10708A (6) (1.0 g, 4.17 mmol) was mixed with some EtOH to give a slurry. Sodium ethoxide (4.2 mL, 1 M) in ethanol was added and the solvent was evaporated. The mixture was heated at 120° C. for 20 h and the reaction was followed by PDMS. The crude product was recrystallized from DMF, filtered and washed with acetone and water. During recrystallization the ester had been hydrolyzed and the product obtained was the corresponding acid. $^1$H NMR (DMSO) δ 2.25 (s, 6H), 3.20 (s, 2H), 7.09 (s, 2H) and 7.53 (m, 5 H).

Example 12

2-[(5,6-Dimethyl-2-benzoimidazolyl)amino]-4-hydroxy-6-trifluorometyl-5-pyrimidine acetic acid (10)

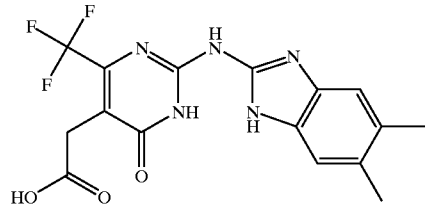

Diethyl-2-trifluoroacetyl succinate (0.40 g, 1.5 mmol) and 2-guanidino-5,6-dimethyl-benzimidazole (6) (0.35 g, 1.5 mmol) was mixed with some EtOH to give a slurry. Sodium ethoxide (1.5 mL, 1 M) in ethanol was added and the solvent was evaporated. The mixture was heated at 100° C. for 4 h, followed by 1 h heating at 150° C. The reaction was followed by PDMS. The crude product was recrystallized from DMF (5 mL), filtered and washed with acetone and water. During recrystallization the ester had been hydrolyzed and the product obtained was the corresponding acid. Gave 0.23 g as mixture of acid and ester. 50 mg was hydrolyzed in NaOH (50 mL, 1 M). The solution was then acidified and the precipitated product was collected to give 30 mg. $^1$H NMR (DMSO) δ 2.27 (s, 6H), 3.43 (s, 2H) and 7.18 (s, 2H).

Example 13

2-[(5,6-Dimethyl-2-benzoimidazolyl)amino]-4-hydroxy-6-isopropyl-5-pyrimidine acetic acid, (11)

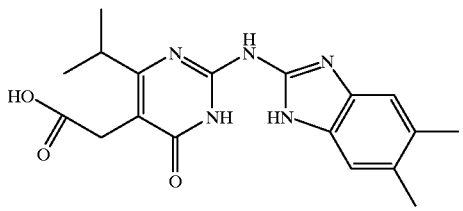

2-Guanidino-5,6-dimethyl-benzimidazole, (6) (1.24 g, 5.17 mmol) was dissolved in EtOH and ethoxide (5.2 mL. 1 M) in ethanol was added. The salt formed was filtered and diethyl-2-isobutyryl succinate (1.86 g, 7.6 mmol) was added and the solvent was then evaporated. The mixture was heated at 150° C. for 4 h and the reaction was followed by PDMS. The crude product was recrystallized from DMF, filtered and washed with acetone and water. The product was hydrolyzed in NaOH (50 mL. 1 M). acidified with HCl and the precipitate was collected. The product was recrystallized from DMSO (5 mL), filtered and washed with water and acetone to give 54 mg. $^1$H NMR (DMSO) δ 1.19 (d, 6H), 2.23 (s, 6H), 3.01 (q, 1H), 3.33 (s, 2H) and 7.09 (s, 2H).

Example 14

Methyl-2-[(5,6-Dimethyl-2-benzoimidazolyl)amino]-1,4-dimethyl-6-oxo-5-pyrimidinyl acetate, (12)

(i) 4-Hydroxy-6-methyl-5-pyrimidine acetic acid,

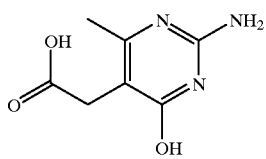

Guanidine hydrochloride (4.0 g, 42 mmol) was added to sodium ethoxide in ethanol (60 mL, 1 M) and the solution was stirred for 10 min. Diethylacetylsuccinate (9.0 g, 42 mmol) was added and the solution was refluxed for 4 h and then stirred over night at room temperature. Water (20 mL) was added to the mixture and the product was filtered and washed with water and EtOH. Yield: 4.2 g (55%). $^1$H NMR (DMSO) δ 2.00 (s, 3H) and 3.22 (s, 2H).

(ii) Methyl-2-[(di-(S)-methylthio)carbonimido]-N-methyl-4-oxo-6-methyl-5-pyrimidine acetate

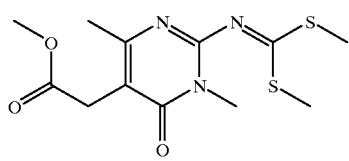

4-Hydroxy-6-methyl-5-pyrimidine acetic acid (1.0 g, 5.5 mmol) was mixed with DMF (150 mL). NaOH (6 mL, 20 M) was added and the mixture was allowed to cool and CS$_2$ (10 mL) was added. The dark red mixture was stirred for 30 min. followed by addition of MeI (10 mL). The colour changed to yellow and the mixture was stirred for 2 h. TThe reaction mixture was partitioned between water and methylene chloride and the organic phase was dried and evaporated. The crude product was purified on silica gel with a gradient of toluene:EtOAc (100% toluene-50% toluene). Yield: 75 mg. (4%) $^1$H NMR (DMSO) δ 2.18 (s, 3H), 2.58 (s, 6H), 3.41 (s, 3H), 3.50 (s, 2H) and 3.58 (s, 3H).

(iii) Methyl-2-[(5,6-Dimethyl-2-benzoimidazolyl)amino]-1,4-dimethyl-6-oxo-5-pyrimidinyl acetate, (12)

(12)

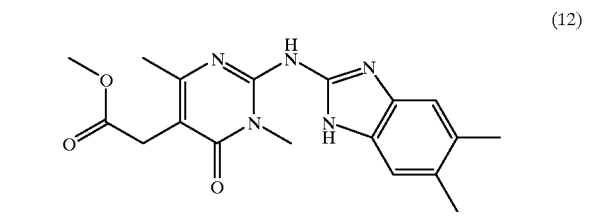

Methyl-2-[(di-(S)-methyltlhio)carbonimido]-N-methyl-4-oxo-6-methyl-5-pyrimidine acetate (34 mg, 0.108 mmol) was dissolved in DMF (1 mL). A solution of 4,5-dimethyl-1,2-phenylenediamine (16 mg, 0.117 mmol) in a few drops of DMF was added and the solution was heated at 100° C. for 1 h and at 150° C. for 1 h more. The solution was allowed to cool and the solvent was evaporated. The product was purified on silica gel with chloroform:acetone:formic acid (gradient 96:3:1–89:10:1). Yield: 19 mg. (50%)

Mp: 272–274° C.

Example 15

2-{4-methyl-6-oxo-2-[(1,5,6-trimethyl-1H-benzimidazol-2-yl)amino]-1,6-dihydro-5-pyrimidinyl}acetic acid

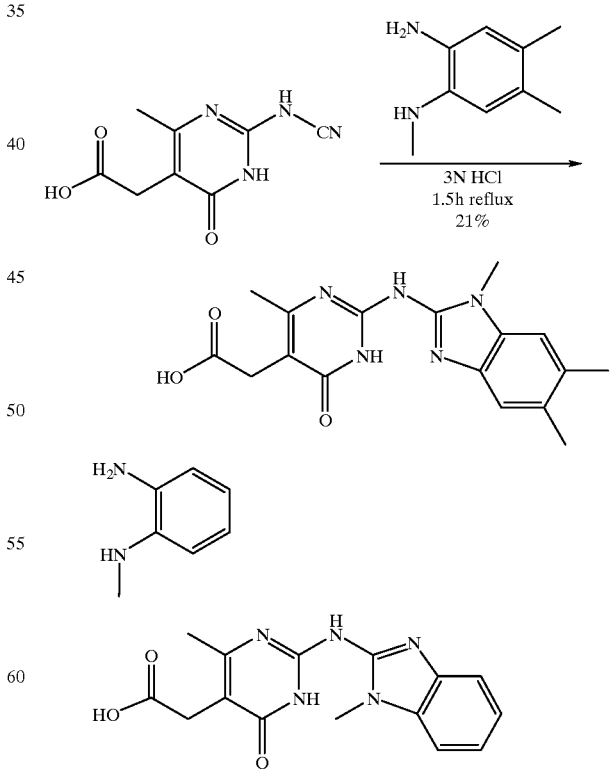

A suspension of N,4,5-trimethylplhenylene-1,2-diamine (541 mg, 3.6 mmol) and (2-cyanoamino)-4-hydroxy-6- methyl-5-pyrimidineacetic acid (625 mg, 3.0 mmol) in 3N aqueous HCl was refluxed (bath 160° C.) for 90 minutes. The heating was switched off and the reaction mixture was left to cool down over night. The white solid that had formed was isolated by filtration, washed with cold water and dried in vacuum over $P_2O_5$. The very insoluble off-white solid (213 mg, 21%) was suspended in a small amount of water and the pH was raised to 7.0 (from 2.0) by addition of an aqueous solution of NaOH. The mixture was concentrated and dried yielding a brownish solid. $^1H$ NMR (DMSO) δ 2.16 (s, 3H, CH3), 2.27 (s, 3H, CH3), 2.30 (s, 3H, CH3), 3.18 (s, 2H, CH2), 3.58 (s, 3H, N—CH3), 7.12 (s, 1H, CH), 7.26 (s, 1H, CH); $^{13}C$ NMR (DMSO) δ 19.9, 28.0, 31.7, 109.1, 115.0, 129.1. 130.6, 153.3, 163.), 173.0, MS (EI+, [M]$^+$) m/z 341; Anal. Calcd. (found) for $C_9H_{14}N_2$ (incl. 1.7 eq. NaOH): C 50.00 (49.88)% H 5.00 (5.10)% N 17.11 (16.90)%.

BIOLOGICAL ACTIVITY

Example 16

Dimerisation Assay

A slightly modified fluoresence quenching assay previously described by Cunningham B C et al., 1991, Science 254, 821–825 was used.

Hormone induced receptor oligomerization via the formation of a 1:2 complex with the extracellular domain of its receptor or binding protein (hGHbp) has been identified as a first critical step in hGH signal transduction. The binding of hGH to recombinantly expressed hGHbp which has been labeled with a flourescent label such as rhodamine results in a diminished signal. A small modecule which mimics the quench induced upon hGH binding in this assay may also mimic the full biological effects of native hormone.

Materials and Methods

The protein reagents used in this assay were recombiniantly produced in E. Coli. These included the hGH, reference active, and a modified form of hGHbp. The modification was used to facilitate labeling and consisted of hGHbpGly$_4$Cys. This is hereinafter designated hGHbp1433. HGHbp1433 was subsequently labeled with rhodamine, hereinafter designated rho-hGHbp.

Results

Figure 3:
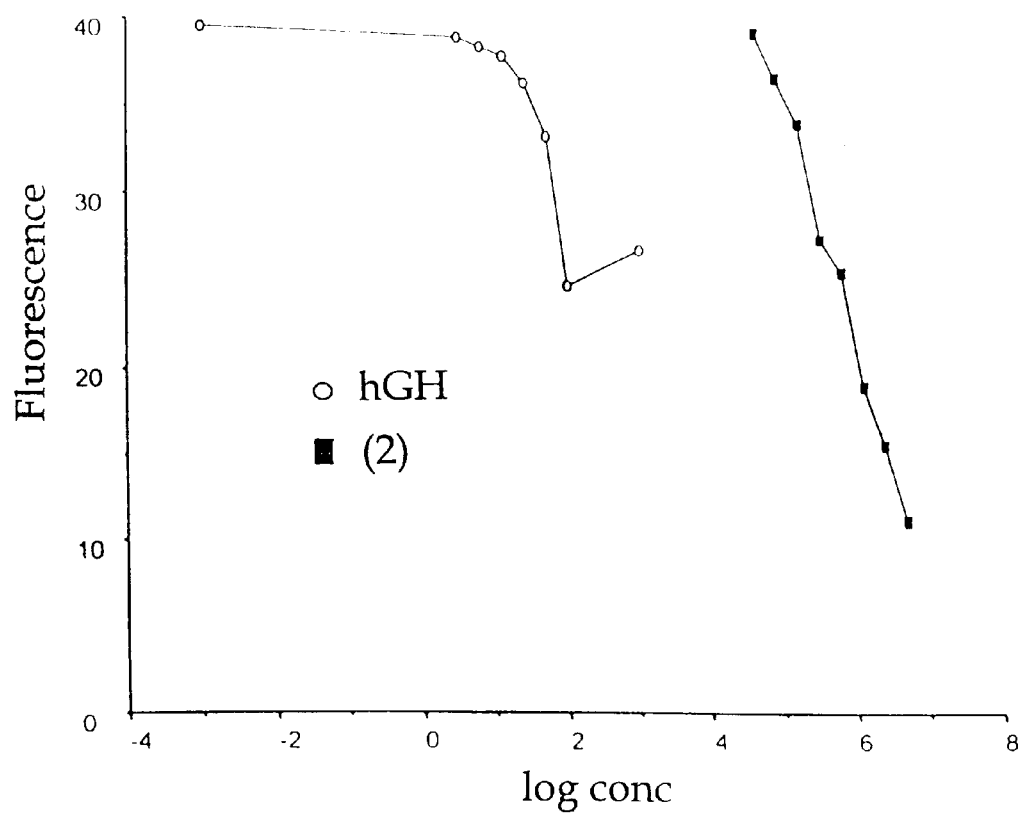
FIG. 3 illustrates dose response curves of hGH and compound (2) in dimerisation assay.

In FIG. 3 the effects on fluorescence quenching in dimerisation assay is shown for hGH and (2). In both cases clear dose response curves could be detected in repeated experiments.

Example 17

Glucose uptake.

Materials and Methods

Cell culture. AT-1 cells from left atrial-derived transplantable tumors were established in primary cultures as earlier described by Steinhelper M. E et al,. Am. J. Physiol. 259, 1826–1834, 1990.

Glucose transport. Glucose transport was assayed as described by Hundal et al Biochem J. 297, 289–295, 1994.

Cells were kept in low glucose DMEM without serum for 5 hours prior hormone addition. After incubation with hormones for 60 minutes if not otherwise stated cell monolayers were rinsed with PBS. Glucose uptake was quantified by incubating the cells in the presence of 0.1 Ci/ml $^3$H-2-deoxy-glucose in PBS for 4 minutes. Non specific uptake was determined by quantifying cell associated radioactivity in the presence of 20 uM CytochalasinB. Uptake of $^3$H-2-deoxy-glucose was terminated by rapidly aspirating the medium followed by two successive washes with ice cold PBS. The cells were lysed in 0.5 M NaOH and followed by liquid scintillation counting. Rates of transport were normalized for protein content in each well.

Materials. Female B6D2/F1 mice were purchased from Bomholt Gård. Denmark. At-1 cells was provided by dr. W. Claycomb, Louisiana State University Medical Center, New Orleans, La.

Joklik's MEM, Dulbecko's MEM, Pen/Strep and Foetal Calf Serum (FCS) and all plastic ware were from Life Technologies. Collagenase was from Worthington biochemical Corp. and Trypsin (pig pancreas) from US Biochemical Corp. USA. $^3$H-2-deoxy-glucose was from Du Pont NEN. duMedical Scandinavia, Sweden. Human Growth Hormone, Genotropin batch 68199-51 was from Pharmacia&Upjohn, Sweden. CytochalasinB, bovine insulin and Wortmannin were from Sigma.

Results

Figure 4:
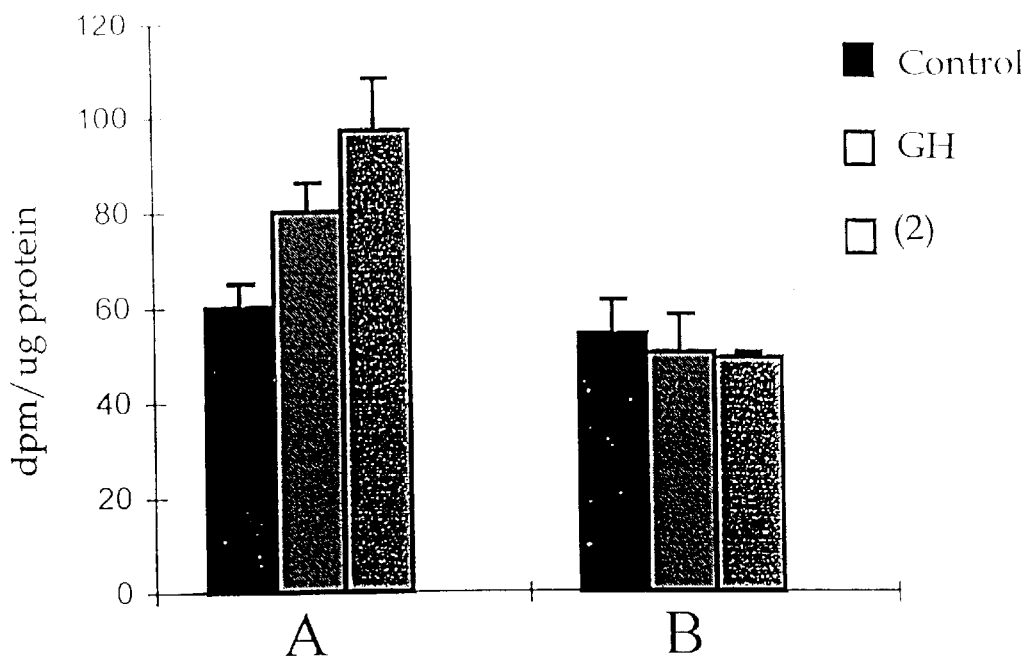
FIG. 4 illustrates glucose uptake in cardiac myocites treated with medium (control), hGH (x nM) and compound (2) (10 mM).

When 10 uM of the compound (2) was incubated for 1 hour prior glucose transport measurement the substance increased glucose transport to the same extent as GH (FIG. 4A). When cardiomyocytes were incubated with 1 uM Wortmannin together with hGH or the compound for 60 minutes prior transport measurements, the wortmannin treated cells did not respond with increased glucose transport (FIG. 4B). This was due to an inhibition of a signal generated from the receptor by inhibiting the signal transducer phosphoinositide 3-kinase (PI 3-kinase).

What is claimed is:

1. A compound of the formula (I)

(I)

wherein Y—X is >C═X and X is NR8, O, or S and R2 is H, $C_1$–$C_8$ alkyl, substituted $C_1$–$C_8$ alkyl(Ring) or substituted Ring; or Y—X is >C—X and X is H, $C_1$–$C_8$ alkyl, substituted $C_1$–$C_8$ alkyl, Ring, substituted Ring, OR9 or NHR9 and R2 is a bond to Y;

Z is O, S or NR12;

R1 is H, methyl, propyl, butyl, substituted $C_1$–$C_8$ alkyl, Ring or substituted Ring;

R3 is H, $C_1$–$C_8$ alkyl, substituted $C_1$–$C_8$ alkyl, Ring, substituted Ring, OR9 or NHR9;

R4, R5, R6 and R7 are H, halogen, OR10, NR10, R11, NO2, CF3, CN, COR8, COOR8, CONHR8 and/or N3 in any combination, and/or two adjacent R4, R5, R6 or R7 form Ring; and R8, R9, R10, R11, R12 and R13 are H, $C_1$–$C_8$ alkyl, substituted $C_1$–$C_8$ alkyl(Ring), Ring and/or substituted Ring in any combination; and wherein Ring is a $C_5$–$C_{12}$ ring, optionally including one or two ring heteroatoms selected from the group consisting of O, S and N, and the substituents for the substituted groups are individually selected from the group consisting of halogen, OH, $C_1$–$C_8$ alkyl, OR10, NR10, R11, NO2, CF3, CN, COR8 and COOR8.

2. Compound according to claim 1, wherein alkyl is straight or branched chain with 1 to 4 carbon, and the substituents are individually selected from the group consisting of —OH, $C_1$–$C_4$ alkyl, O-Ring, nitro, halogen and carboxy.

3. Compound according to claim 1, wherein Z is NH.

4. A compound of the formula (I)

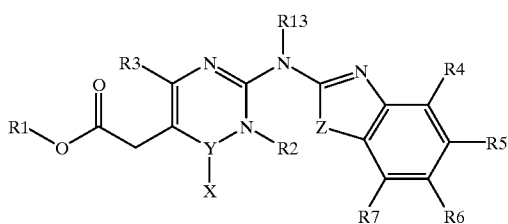

(I)

wherein Y—X is >C=X and X is NR8, O, or S and R2 is H, $C_1$–$C_8$ alkyl, substituted $C_1$–$C_8$ alkyl(Ring) or substituted Ring; or Y—X is >C—OH and R2 is a bond to Y;

Z is O, S or NR12;

R1 is H, $C_1$–$C_8$ alkyl, substituted $C_1$–$C_8$ alkyl, Ring or substituted Ring;

R3 is H, $C_1$–$C_8$ alkyl, substituted $C_1$–$C_8$ alkyl, Ring, substituted Ring, OR9 or NHR9;

R4 is halogen, OR10, NR10, $C_1$–$C_8$ alkyl, substituted $C_1$–$C_8$ alkyl(Ring), Ring, substituted Ring, NO2, CF3, CN, COR8, COOR8, CONHR8 and/or N3 in any combination;

R5, R6 and R7 are H, halogen, OR10, NR10, R11, NO2, CF3, CN, COR8, COOR8, CONHR8 and/or N3 in any combination, and/or two adjacent R4, R5, R6 or R7 form Ring; and R8, R9, R10, R11, R12 and R13 are H, $C_1$–$C_8$ alkyl, substituted $C_1$–$C_8$ alkyl(Ring), Ring and/or substituted Ring in any combination; and wherein Ring is a $C_5$–$C_{12}$ ring, optionally including one or two ring heteroatoms selected from the group consisting of O, S and N, and the substituents for the substituted groups are individually selected from the group consisting of halogen, OH, $C_1$–$C_8$ alkyl, OR10, NR10, R11, NO2, CF3, CN, COR8 and COOR8.

5. Compound according to claim 4, wherein Z is NH.

6. A compound of the formula (I)

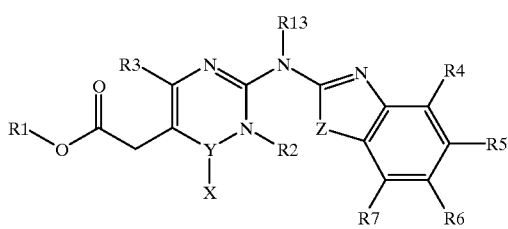

(I)

wherein Y—X is >C=X and X is NR8, O, or S and R2 is H, $C_1$–$C_8$ alkyl, substituted $C_1$–$C_8$ alkyl(Ring) or substituted Ring; or Y—X is >C—OH and R2 is a bond to Y;

Z is O, S or NR12;

R1 is H, $C_1$–$C_8$ alkyl, substituted $C_1$–$C_8$ alkyl, Ring or substituted Ring;

R3 is H, $C_1$–$C_8$ alkyl, substituted $C_1$–$C_8$ alkyl, Ring, substituted Ring, OR9 or NHR9;

R5 is halogen, OR10, NR10, $C_1$–$C_8$ alkyl, substituted $C_1$–$C_8$ alkyl(Ring), Ring, substituted Ring, NO2, CF3, CN, COR8, COOR8, CONHR8 and/or N3 in any combination;

R4, R6 and R7 are H, halogen, OR10, NR10, R11, NO2, CF3, CN, COR8, COOR8, CONHR8 and/or N3 in any combination, and/or two adjacent R4, R5, R6 or R7 form Ring; and R8, R9, R10, R11, R12 and R13 are H, $C_1$–$C_8$ alkyl, substituted $C_1$–$C_8$ alkyl(Ring), Ring and/or substituted Ring in any combination; and wherein Ring is a $C_5$–$C_{12}$ ring, optionally including one or two ring heteroatoms selected from the group consisting of O, S and N, and the substituents for the substituted groups are individually selected from the group consisting of halogen, OH, $C_1$–$C_8$ alkyl, OR10, NR10, R11, NO2, CF3, CN, COR8 and COOR8.

7. Compound according to claim 6, wherein Z is NH.

8. A compound of the formula (I)

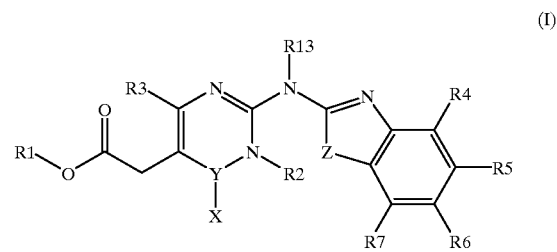

(I)

wherein Y—X is >C=X and X is NR8, O, or S and R2 is H, $C_1$–$C_8$ alkyl, substituted $C_1$–$C_8$ alkyl(Ring) or substituted Ring; or Y—X is >C—OH and R2 is a bond to Y;

Z is O, S or NR12;

R1 is H, $C_1$–$C_8$ alkyl, substituted $C_1$–$C_8$ alkyl, Ring or substituted Ring;

R3 is H, $C_1$–$C_8$ alkyl, substituted $C_1$–$C_8$ alkyl, Ring, substituted Ring, OR9 or NHR9;

R6 is halogen, OR10, NR10, $C_1$–$C_8$ alkyl, substituted $C_1$–$C_8$ alkyl(Ring), Ring, substituted Ring, NO2, CF3, CN, COR8, COOR8, CONHR8 and/or N3 in any combination;

R4, R5 and R7 are H, halogen, OR10, NR10, R11, NO2, CF3, CN, COR8, COOR8, CONHR8 and/or N3 in any combination, and/or two adjacent R4, R5, R6 or R7 form Ring; and R8, R9, R10, R11, R12 and R13 are H, $C_1$–$C_8$ alkyl, substituted $C_1$–$C_8$ alkyl(Ring), Ring and/or substituted Ring in any combination; and wherein Ring is a $C_5$–$C_{12}$ ring, optionally including one or two ring heteroatoms selected from the group consisting of O, S and N, and the substituents for the substituted groups are individually selected from the group consisting of halogen, OH, $C_1$–$C_8$ alkyl, OR10, NR10, R11, NO2, CF3, CN, COR8 and COOR8.

9. Compound according to claim 8, wherein Z is NH.

10. A compound of the formula (I)

[Structure: Formula (I) showing a pyrimidine ring connected via NR2/N-R13 linkage to a benzimidazole-type ring with substituents R1-O-C(O)-CH2-, R3, R4, R5, R6, R7, X, Y, Z]

wherein Y—X is >C=X and X is NR8, O, or S and R2 is H, $C_1$–$C_8$ alkyl, substituted $C_1$–$C_8$ alkyl(Ring) or substituted Ring; or Y—X is >C—OH and R2 is a bond to Y;

Z is O, S or NR12;

R1 is H, $C_1$–$C_8$ alkyl, substituted $C_1$–$C_8$ alkyl, Ring or substituted Ring;

R3 is H, $C_1$–$C_8$ alkyl, substituted $C_1$–$C_8$ alkyl, Ring, substituted Ring, OR9 or NHR9;

R4, R5 and R6 are H, halogen, OR10, NR10, R11, NO2, CF3, CN, COR8, COOR8, CONHR8 and/or N3 in any combination, and/or two adjacent R4, R5, R6 or R7 form Ring;

R7 is halogen, OR10, NR10, $C_1$–$C_8$ alkyl, substituted $C_1$–$C_8$ alkyl(Ring), Ring, substituted Ring, NO2, CF3, CN, COR8, COOR8, CONHR8 and/or N3 in any combination; and R8, R9, R10, R11, R12 and R13 are H, $C_1$–$C_8$ alkyl, substituted $C_1$–$C_8$ alkyl(Ring), Ring and/or substituted Ring in any combination; and wherein Ring is a $C_5$–$C_{12}$ ring, optionally including one or two ring heteroatoms selected from the group consisting of OP, S and N, and the substituents for the substituted groups are individually selected from the group consisting of halogen, OH, $C_1$–$C_8$ alkyl, OR10, NR10, R11, NO2, CF3, CN, COR8 and COOR8.

11. Compound according to claim 10, wherein Z is NH.

12. Compound selected from the group consisting of 2-[(5,6-Dimethyl-2-benzoimidazolyl)amino]-4-hydroxy-6-methyl-5-pyrimidine acetic acid, ethyl ester (1);

2-[(5,6-Dimethyl-2-benzoimidazolyl)amino]-4-hydroxy-6-methyl-5-pyrimidine acetic acid (2);

2-[(5,6-Dimethyl-2-benzoimidazolyl)anino]-4-hydroxy-6-phenyl-5-pyrimidine acetic acid (9);

2-[(5,6-Dimethyl-2-benzoimidazoiyl)amino]-4-hydroxy-6-trifluoromethyl-5-pyrimidine acetic acid (10);

2-[(5,6-Dinethyl-2-benzoimidazolyl)amino]-4-hydroxy-6-isopropyl-5-pyrimidine acetic acid, (11); and Methyl-2-[(5,6-Dimethyl-2-benzoimidazolyl)amino-]1,4-dimethyl-6-oxo-5-pyrimidinyl acetate, (12).

13. A pharmaceutical composition comprising a compound according to claim 1 and a pharmaceutically acceptable carrier.

14. Method for the preparation of a compound according to claim 1, comprising reacting a cyanoamine pyrimidine acetic acid together with 1,2-phenylene diamine, 2-amino thiophenol or 2-amino phenol.

15. Method for the preparation of a compound according to claim 1, comprising reacting 2-guanidino-benzoimidazole with diethyl acetylsuccinate.

16. A process for the preparation of a pharmaceutical composition according to claim 13, comprising mixing the compound of formula (I) and the pharmaceutically acceptable carrier.

17. Method for wound healing or treatment of growth hormone deficiency, Turner Syndrome, infertility, dystrophy, osteoporosis or lactation failure, comprising administering a therapeutic dose of a compound according to claim 4.

18. Method for wound healing or treatment of growth hormone deficiency, Turner Syndrome, infertility, dystrophy, osteoporosis or lactation failure, comprising administering a therapeutic dose of a compound according to claim 6.

19. Method for wound healing or treatment of growth hormone deficiency, Turner Syndrome, infertility, dystrophy, osteoporosis or lactation failure, comprising administering a therapeutic dose of a compound according to claim 8.

20. Method for wound healing or treatment of growth hormone deficiency, Turner Syndrome, infertility, dystrophy, osteoporosis or lactation failure, comprising administering a therapeutic dose of a compound according to claim 10.

21. Method for wound healing or treatment of growth hormone deficiency, Turner Syndrome, infertility, dystrophy, osteoporosis or lactation failure, comprising administering a therapeutic dose of a compound of the formula (I)

[Structure: Formula (I) as above]

wherein

Y—X is >C=X and X is NR8, O, or S and R2 is H, $C_1$–$C_8$ alkyl, substituted $C_1$–$C_8$ alkyl(Ring) or substituted Ring; or Y—X is >C—X and X is H, $C_1$–$C_8$ alkyl, substituted $C_1$–$C_8$ alkyl, Ring, substituted Ring, OR9 or NHR9 and R2 is a bond to Y;

Z is O, S or NR12;

R1 is H, $C_1$–$C_8$ alkyl, substituted $C_1$–$C_8$ alkyl, Ring or substituted Ring;

R3 is H, $C_1$–$C_8$ alkyl, substituted $C_1$–$C_8$ alkyl, Ring, substituted Ring, OR9 or NHR9;

R4, R5, R6 and R7 are H, halogen, OR10, NR10, R11, NO2, CF3, CN, COR8, COOR8, CONHR8 and/or N3 in any combination and/or two adjacent R4, R5, R6 or R7 form Ring; and R8, R9, R10, R11, R12 and R13 are H, $C_1$–$C_8$ alkyl, substituted $C_1$–$C_8$ alkyl(Ring), Ring and/or substituted Ring in any combination; and wherein Ring is a $C_5$–$C_{12}$ ring, optionally including one or two ring heteroatoms selected from the group consisting of O, S and N, and the substituents for the substituted groups are individually selected from the group consisting of halogen, OH, $C_1$–$C_8$ alkyl, OR10, NR10, R11, NO2, CF3, CN, COR8 and COOR8.

22. Method according to claim 21, wherein alkyl is straight or branched chain with 1 to 4 carbon, and the substituents are individually selected from the group consisting of —OH, $C_1$–$C_4$ alkyl, O-Ring, nitro, halogen and carboxy.

23. Method according to claim 21, wherein Z is NH.

24. Method for wound healing and/or treatment of glaucoma deficiency, Turner Syndrome, infertility, dystrophy, osteoporosis and/or lactation failure, comprising administering a therapeutic dose of a compound selected from the group consisting of 2-[(5,6-Dimethyl-2-benzoimidazolyl)amino]-4-hydroxy-6-methyl-5-pyrimidine acetic acid, ethyl ester (1);

2-[(5,6-Dimethyl-2-benzoimidazolyl)amino]-4-hydroxy-6-methyl-5-pyrimidine acetic acid (2);

2-[(5,6-Dimethyl-2-benzoimidazolyl)amino]-4-hydroxy-6-phenyl-5-pyrimidine acetic acid (9);

2-[(5,6-Dimethyl-2-benzoimidazolyl)amino]-4-hydroxy-6-trifluoromethyl-5-pyrimidine acetic acid (10);

2-[(5,6-Dimethyl-2-benzoimidazolyl)amino]-4-hydroxy-6-isopropyl-5-pyrimidine acetic acid (11); and Methyl-2-[(5,6-Dimethyl-2-benzoimidazolyl)amino]-1,4-dimethyl-6-oxo-5-pyrimidinyl acetate (12).

25. Method for wound healing or treatment of growth hormone deficiency, Turner Syndrome, infertility, dystrophy, osteoporosis or lactation failure, comprising administering a therapeutic dose of a compound according to claim 1.

26. Method for wound healing or treatment of growth hormone deficiency, Turner Syndrome, infertility, dystrophy, osteoporosis or lactation failure, comprising administering a therapeutic dose of a pharmaceutical composition according to claim 13.

* * * * *

UNITED STATES PATENT AND TRADEMARK OFFICE
CERTIFICATE OF CORRECTION

PATENT NO.    : 6,329,383 B1
DATED         : December 11, 2001
INVENTOR(S)   : Charles Hedgecock et al.

It is certified that error appears in the above-identified patent and that said Letters Patent is hereby corrected as shown below:

<u>Column 23, claim 12,</u>
Line 46, change "anino" to -- amino --;
Line 48, change "benzoimidazoiyl" to -- benzoimidazolyl --;
Line 50, change "Dinethyl" to -- Dimethyl --.

Signed and Sealed this

Sixteenth Day of April, 2002

Attest:

JAMES E. ROGAN
*Attesting Officer*          *Director of the United States Patent and Trademark Office*